United States Patent
Jung et al.

(10) Patent No.: US 12,337,198 B2
(45) Date of Patent: Jun. 24, 2025

(54) ULTRASOUND GENERATION DEVICE CAPABLE OF ADJUSTING ULTRASOUND FOCUS DEPTH

(71) Applicant: JEISYS MEDICAL INC., Seoul (KR)

(72) Inventors: Kwang Hyeok Jung, Seoul (KR); Won Ju Yi, Seoul (KR); Dong Hwan Kang, Seoul (KR)

(73) Assignee: Jeisys Medical Inc., Seoul (KR)

( * ) Notice: Subject to any disclaimer, the term of this patent is extended or adjusted under 35 U.S.C. 154(b) by 165 days.

(21) Appl. No.: 18/335,312

(22) Filed: Jun. 15, 2023

(65) Prior Publication Data
US 2023/0321461 A1    Oct. 12, 2023

Related U.S. Application Data

(63) Continuation of application No. PCT/KR2021/012730, filed on Sep. 16, 2021.

(30) Foreign Application Priority Data

Jan. 22, 2021    (KR) .................. 10-2021-0009371

(51) Int. Cl.
*A61N 7/02*    (2006.01)
*A61N 7/00*    (2006.01)

(52) U.S. Cl.
CPC ......... *A61N 7/02* (2013.01); *A61N 2007/0034* (2013.01); *A61N 2007/0091* (2013.01)

(58) Field of Classification Search
CPC .............. A61N 7/02; A61N 2007/0034; A61N 2007/0091; A61N 2007/0065; A61N 2007/025

See application file for complete search history.

(56) References Cited

U.S. PATENT DOCUMENTS 12,090,347 B2 * 9/2024 Lee .................... A61N 7/02
2019/0366129 A1   12/2019 Park et al.

FOREIGN PATENT DOCUMENTS

KR   10-2015-0115432 A   10/2015
KR   10-2016-0063119 A    6/2016
(Continued)

OTHER PUBLICATIONS

International Search Report issued in PCT/KR2021/012730; mailed Dec. 30, 2021.

*Primary Examiner* — Hien N Nguyen
(74) *Attorney, Agent, or Firm* — Leydig, Voit & Mayer, Ltd.

(57) ABSTRACT

The present invention relates to an ultrasound generation device capable of adjusting an ultrasound focus depth, comprising: a handpiece; a cartridge housing detachably coupled to the handpiece; an ultrasonic wave-generating unit provided in the handpiece or the cartridge housing; a rotating unit of which the outer circumferential surface makes contact with a support unit of the ultrasonic wave-generating unit, and which has a shape of a section with a rotation radius gradually increased from the center of the rotating unit; and a rotation adjusting unit coupled to the rotating unit to apply force for driving the rotating unit, wherein the rotating unit adjusts the focal depth of the ultrasonic waves from the ultrasonic wave-generating unit, as the rotation adjusting unit rotates the rotating unit to change a rotation radius of the rotating unit, such that the ultrasonic wave-generating unit is moved.

13 Claims, 8 Drawing Sheets

(56) References Cited

FOREIGN PATENT DOCUMENTS

| KR | 10-1700334 B1 | 1/2017 |
|----|---------------|--------|
| KR | 10-2017-0074716 A | 6/2017 |
| KR | 10-1750444 B1 | 6/2017 |
| KR | 10-1756618 B1 | 7/2017 |
| KR | 10-2256841 B1 | 5/2021 |

* cited by examiner

ULTRASOUND GENERATION DEVICE CAPABLE OF ADJUSTING ULTRASOUND FOCUS DEPTH

CROSS-REFERENCE TO RELATED APPLICATIONS

The present application is a continuation of International Patent Application No. PCT/KR2021/012730, filed on Sep. 16, 2021, which is based upon and claims the benefit of priority to Korean Patent Application No. 10-2021-0009371 filed on Jan. 22, 2021. The disclosures of the above-listed applications are hereby incorporated by reference herein in their entirety.

BACKGROUND

Embodiments of the inventive concept relate to a device for generating ultrasonic waves to adjust a focal depth of the ultrasonic wave, which includes a handpiece and a cartridge housing detachably coupled to the handpiece to generate the ultrasonic waves.

Ultrasonic waves, which refer to waves having the frequency of 20 kHz or more, may be variously utilized in not only a medical field of diagnosing and treating an affected part, but also skin beauty.

In particular, high intensity focus ultrasound (HIFU), which focuses ultrasound waves with high intensity, non-invasively focuses the ultrasound waves to a specific depth of the skin surface without any damage to the skin surface, which is different from a laser beam and a radio frequency. Accordingly, as temperature is rapidly increased at the target depth of the skin, and the coagulation necrosis of cells is caused in various affected parts of the skin without side effects. These necrotized cells are naturally removed through the repair mechanism for the damaged part of the body.

Meanwhile, a conventional ultrasonic waves generating device has a cartridge housing, and an ultrasonic wave-generating unit provided in the cartridge housing to irradiate ultrasonic waves.

The conventional ultrasonic waves generating device may not adjust the focal depth of ultrasonic waves from the ultrasonic wave-generating unit, as the ultrasonic wave-generating unit is fixed into the cartridge housing.

Accordingly, the conventional ultrasonic wave-generating unit may not adjust the focal depth of the ultrasonic waves depending on the target depth of the skin.

SUMMARY

Embodiments of the inventive concept provide a device for generating ultrasonic waves, capable of adjusting the focal depth of the ultrasonic waves depending on the target depth of the skin.

The objects of the inventive concept are not limited to the above, but other effects, which are not mentioned, will be apparently understood to those skilled in the art.

According to an embodiment, a device for generating ultrasonic waves to adjust a focal depth of the ultrasonic wave, includes a handpiece, a cartridge housing detachably coupled to the handpiece, an ultrasonic wave-generating unit provided in the handpiece or the cartridge housing, a rotating unit of which the outer circumferential surface makes contact with a support unit of the ultrasonic wave-generating unit, and which has a shape of a section with a rotation radius gradually increased from the center of the rotating unit, and a rotation adjusting unit coupled to the rotating unit to apply force for driving the rotating unit. The rotating unit adjusts the focal depth of the ultrasonic waves from the ultrasonic wave-generating unit, as the rotation adjusting unit rotates the rotating unit to change a rotation radius of the rotating unit, such that the ultrasonic wave-generating unit is moved.

In addition, the rotation adjusting unit may be one selected from a driving unit, a knob, and an operating button.

In addition, a plurality of contact protrusions may be provided on the outer circumferential surface of the rotating unit, and the support unit of the ultrasonic wave-generating unit making contact with the outer circumferential surface of the rotating unit may have a contact part selectively contact to or separated from the plurality of contact protrusions.

Further, the contact part may be a contact groove recessed in the support unit of the ultrasonic wave-generating unit.

In addition, the device may include a locking unit to lock the rotation of the rotating unit or to release the locking of the rotation of the rotating unit.

In addition, plurality of contact protrusions may protrude with mutually different heights from the outer circumferential surface of the rotating unit.

In addition, the rotating unit may include a restriction protrusion which is locked to the support unit in the outer circumferential surface of the rotating unit to restrict the rotation of the rotating unit while ranging from a minimum rotating radius of the rotating unit to a maximum rotating radius of the rotating unit In addition, the device further includes an elastic unit to generate elastic force for pressing in a direction opposite to one direction of a moving direction of the ultrasonic wave-generating unit.

Further, the device may further include a first frame, and a second frame coupled to the first frame to be movable in the moving direction of the ultrasonic wave-generating unit, and coupled to the ultrasonic wave-generating unit.

Further, the first frame may include a linear track formed in the moving direction of the ultrasonic wave-generating unit, and the second frame may include a linear guide moving along the linear track.

In addition, the elastic unit may be a spring to connect the first frame to the second frame.

Further, the device may further include a driving device provided in the handpiece, and a main shaft having one end coupled to the driving device and an opposite end passing through the first frame. The driving device may move the main shaft in a longitudinal direction of the handpiece.

Other details of the inventive concept are included in the detailed description and accompanying drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

The above and other aspects, features and advantages of the inventive concept will become apparent from embodiments to be described in detail in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the scope of the inventive concept to those skilled in the art. The inventive concept may be defined by the scope of the claims.

The terms used herein are provided to describe embodiments, not intended to limit the inventive concept. In the specification, the singular forms include plural forms unless particularly mentioned. The terms "comprises" and/or "comprising" used herein do not exclude the presence or addition of one or more other components, in addition to the aforementioned components. The same reference numerals denote the same components throughout the specification. As used herein, the term "and/or" includes each of the associated components and all combinations of one or more of the associated components. It will be understood that, although the terms "first", "second", etc., may be used herein to describe various components, these components should not be limited by these terms. These terms are only used to distinguish one component from another component. Thus, a first component that is discussed below could be termed a second component without departing from the technical idea of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, an embodiment of the inventive concept will be described in detail with reference to the accompanying drawings.

Figure 1:
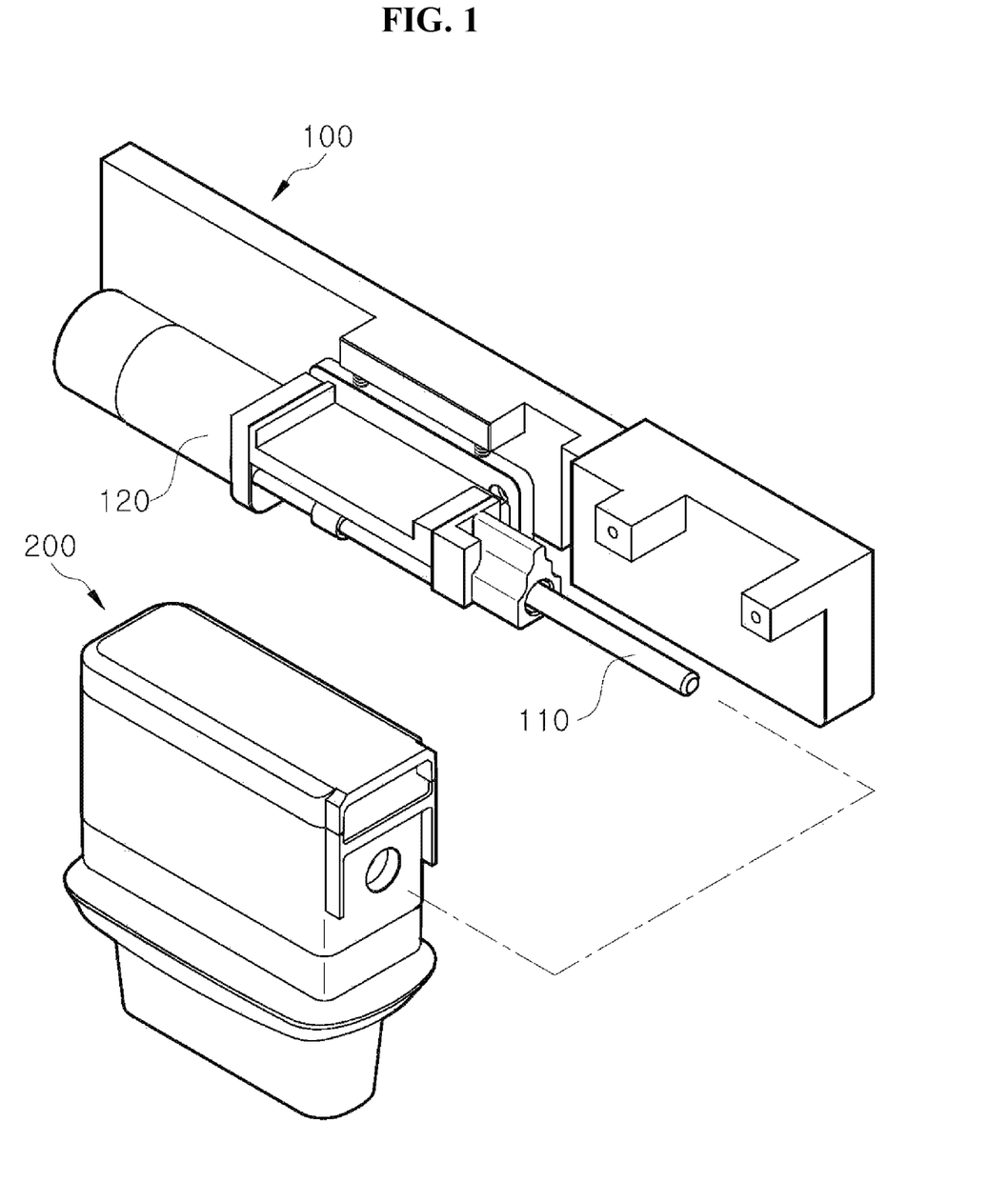
FIG. 1 is a perspective view illustrating a cartridge housing and a handpiece separated from each other in a device for generating ultrasonic waves to adjust a focal depth of ultrasonic waves, according to an embodiment of the inventive concept.
Figure 2:
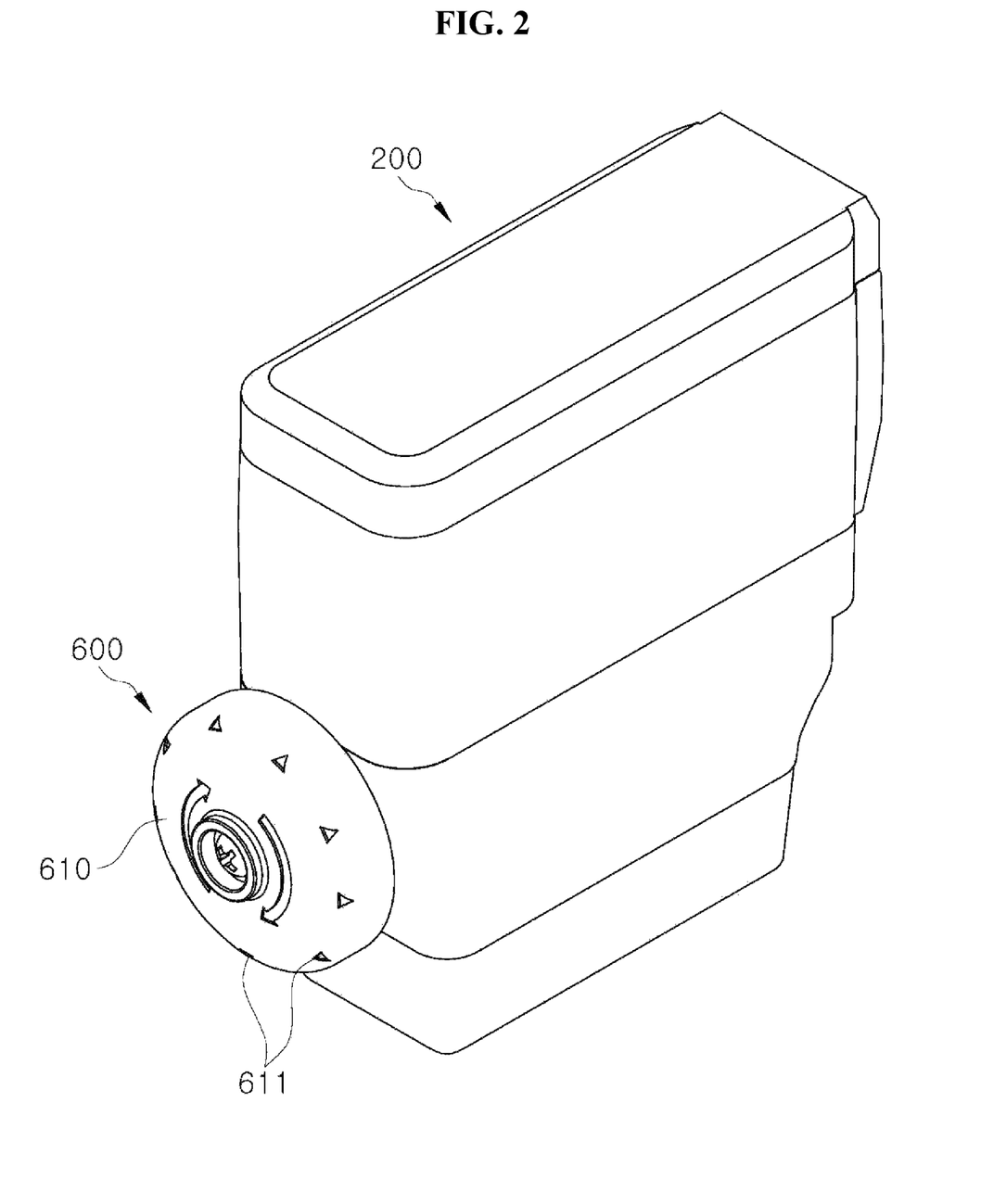
FIG. 2 is a perspective view illustrating a cartridge housing in a device for generating ultrasonic waves to adjust a focal depth of ultrasonic waves, according to an embodiment of the inventive concept.
Figure 3:
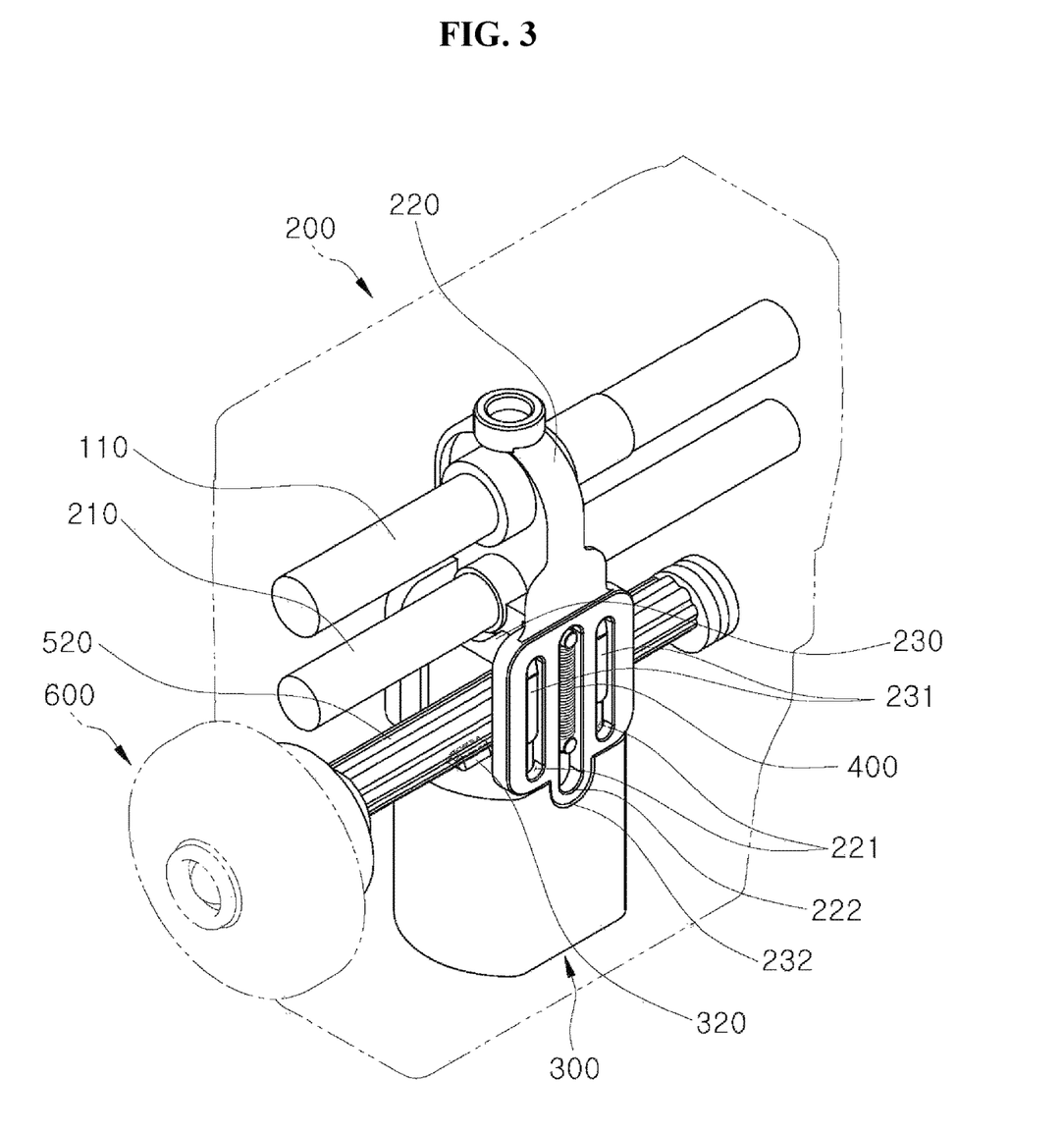
FIG. 3 is a perspective view illustrating a cartridge housing in a device for generating ultrasonic waves to adjust a focal depth of ultrasonic waves, according to an embodiment of the inventive concept.
Figure 4:
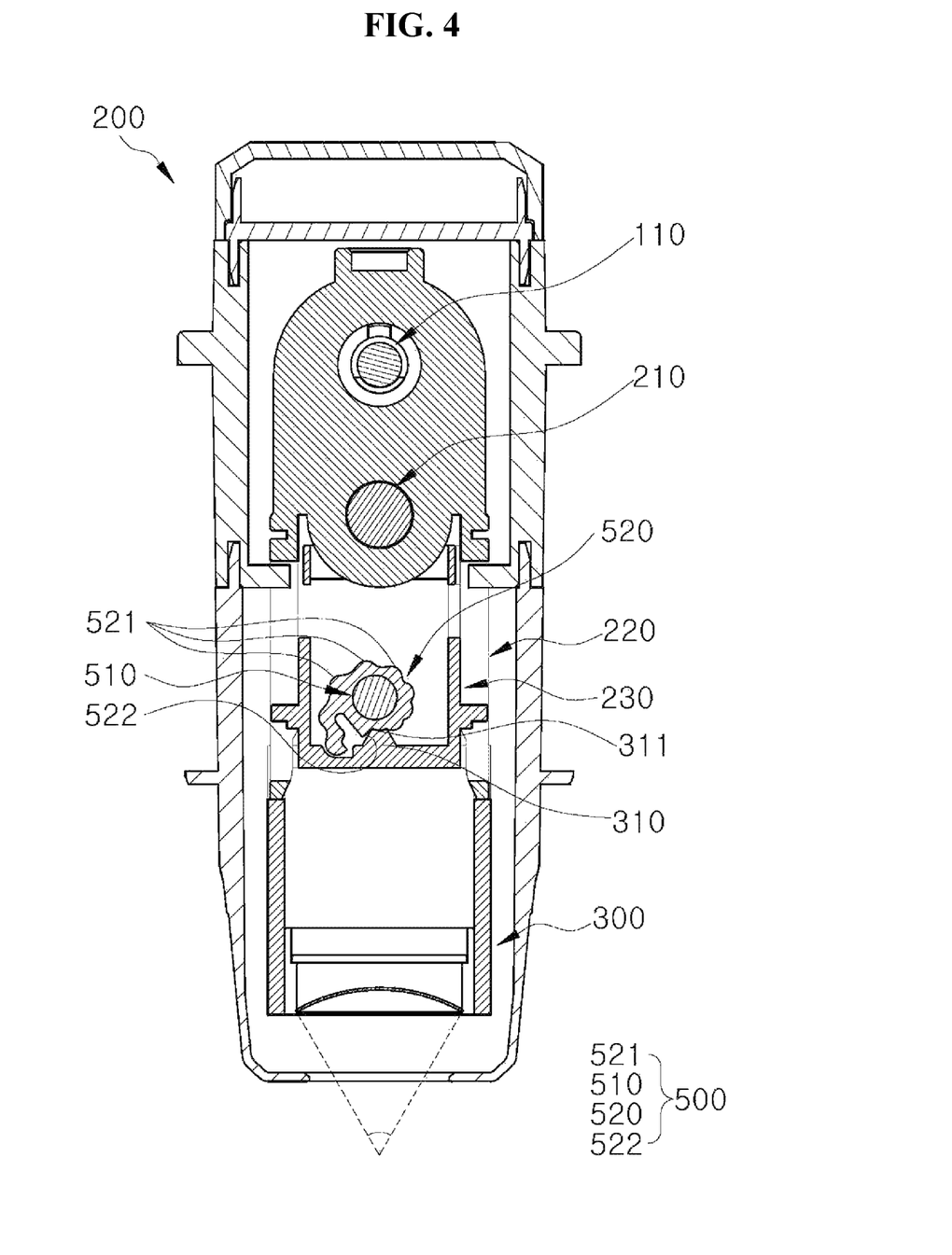
FIG. 4 is a sectional view illustrating a cartridge housing in a device for generating ultrasonic waves to adjust a focal depth of ultrasonic waves, according to an embodiment of the inventive concept.
Figure 5:
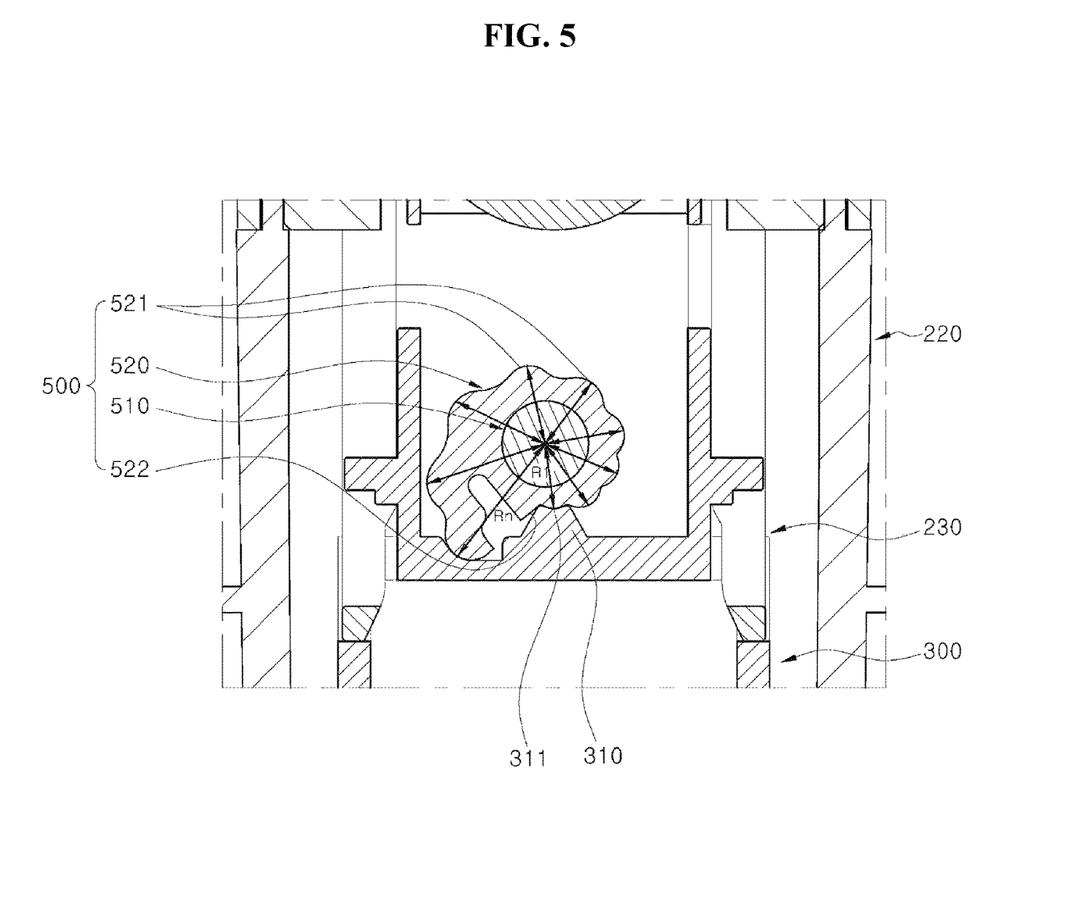
FIG. 5 is an enlarged view illustrating a rotating unit in a device for generating ultrasonic waves to adjust a focal depth of ultrasonic waves, according to an embodiment of the inventive concept.

FIG. 1 is a perspective view illustrating a cartridge housing and a handpiece separated from each other in a device for generating ultrasonic waves to adjust a focal depth of ultrasonic waves, according to an embodiment of the inventive concept, and FIG. 2 is a perspective view illustrating a cartridge housing in a device for generating ultrasonic waves to adjust a focal depth of ultrasonic waves, according to an embodiment of the inventive concept. FIG. 3 is a perspective view illustrating a cartridge housing in a device for generating ultrasonic waves to adjust a focal depth of ultrasonic waves, according to an embodiment of the inventive concept, and FIG. 4 is a sectional view illustrating a cartridge housing in a device for generating ultrasonic waves to adjust a focal depth of ultrasonic waves, according to an embodiment of the inventive concept. FIG. 5 is an enlarged view illustrating a rotating unit in a device for generating ultrasonic waves to adjust a focal depth of ultrasonic waves, according to an embodiment of the inventive concept;

As illustrated in FIGS. 1 to 5, according to the inventive concept, a device for generating the ultrasonic waves to adjust the focal depth of the ultrasonic-wave includes a handpiece 100, a cartridge housing 200, an ultrasonic wave-generating unit 300, an elastic unit 400, a rotating unit 500, and a rotation adjusting unit 600.

The handpiece 100 serving as a basic main body may be utilized as a gripper allowing a user to grip. The cartridge housing 200 having the ultrasonic wave-generating unit 300, which is to be described below, is detachably coupled to one side of the handpiece 100. Accordingly, the user may grip the handpiece 100, move the handpiece 100 to bring the cartridge housing 300 into close contact with the skin surface, and irradiate ultrasonic waves from the ultrasonic wave-generating unit 300 to a target depth of a deep skin part, thereby performing an ultrasonic medical treatment.

The handpiece 100 may have a cable which is provided therein and connected to an RF board to apply RF current to the ultrasonic wave-generating unit 300. The RF board may be received in the cartridge housing 200, and may intermittently or continuously apply the RF current to the ultrasonic wave-generating unit 300.

The handpiece 100 may be coupled to the cartridge housing 200 through a main shaft 110. For example, one end of the main shaft 110 may be coupled to a driving device 120 fixed to the handpiece 100, and an opposite end of the main shaft 110 may be received in the cartridge housing 200. In this case, the opposite end, which is received in the cartridge housing 200, of the main shaft 110 may be fixed to a first frame 220 while passing through the first frame 220. Accordingly, the first frame 220 may be fixed to the cartridge housing 200 through the opposite end of the main shaft 110. The driving device 120 moves in a horizontal direction with respect to a moving direction of the ultrasonic wave-generating unit 300 to be described below.

Meanwhile, a second frame 230, which is to be described below, is detachably coupled to the first frame 220. Accordingly, when the driving device 120 moves the main shaft 110 in a longitudinal direction, the first frame 220, the second frame 230, and the ultrasonic wave-generating unit 300 may move in the longitudinal direction of the main shaft 110, together. For example, the driving device 120 may be a driving motor or an actuator, but the inventive concept is not limited thereto.

In addition, the first frame 220 may be fixed by an auxiliary shaft 210 disposed inside the cartridge housing 200. The auxiliary shaft 210 may be fixed to the first frame 220 while passing through the first frame 220. In addition, opposite ends of the auxiliary shaft 210 may be coupled to opposite surfaces of the cartridge housing 200, respectively. In addition, the main shaft 110 and the auxiliary shaft 210 may be disposed in parallel to each other. In this case, referring to FIG. 3, the main shaft 110 may be disposed above the auxiliary shaft 210.

The cartridge housing 200, which is a kind of a case receiving the ultrasonic wave-generating unit 300, is detachably provided at one side of the handpiece 100.

The cartridge housing 200 may contain a medium for the ultrasonic waves generated from the ultrasonic wave-generating unit 300. For example, the medium may be distilled water, deaeration liquid, or silicone, but the inventive concept is not limited thereto.

The ultrasonic wave-generating unit 300 is disposed inside the handpiece 100 or the cartridge housing 200 to generate ultrasonic waves. The ultrasonic wave-generating unit 300 may include a transducer to focus the ultrasonic waves at a specific position.

The ultrasonic wave-generating unit 300 receives an electronic signal from the RF board through the cable of the handpiece 100 and focuses the ultrasonic waves at the specific position. As described above, the specific position, at which the ultrasonic waves irradiated from the ultrasonic wave-generating unit 300 are focused, may be defined as a focus. In addition, a distance from the distal end of the cartridge housing 200 to the focus of the ultrasonic waves, which are generated from the ultrasonic wave-generating unit 300, may be defined as a focal depth of the ultrasonic waves from the ultrasonic wave-generating unit 300.

The ultrasonic wave-generating unit 300 may be adjusted in the focal depth of the ultrasonic wave, as the cartridge housing 200 moves.

For example, the focal depth of the ultrasonic waves from the ultrasonic wave-generating unit 300 may be adjusted, as the ultrasonic wave-generating unit 300 moves in a direction closer to a rotating shaft 510, which is to be described below, or in a direction farther away from the rotating shaft 510. In detail, the focal depth of the ultrasonic waves from the ultrasonic wave-generating unit 300 may be decreased, as the ultrasonic wave-generating unit 300 moves in the direction closer to the rotating shaft 510. In addition, the focal depth of the ultrasonic waves from the ultrasonic wave-generating unit 300 may be increased, as the ultrasonic wave-generating unit 300 moves in the direction farther away from the rotating shaft 510.

For another example, the focal depth of the ultrasonic waves from the ultrasonic wave-generating unit 300 may be adjusted, as the ultrasonic wave-generating unit 300 moves upward or downward, referring to FIGS. 1 to 5. In detail, as the ultrasonic wave-generating unit 300 moves upward, the focal depth of the ultrasonic waves from the ultrasonic wave-generating unit 300 may be decreased. In addition, the focal depth of the ultrasonic waves from the ultrasonic wave-generating unit 300 may be increased, as the ultrasonic wave-generating unit 300 moves downward.

Hereinafter, for the convenience of explanation, the direction, in which the ultrasonic wave-generating unit 300 is closer to the rotating shaft 510, or the upward direction is defined as "one direction", and the direction, in which the ultrasonic wave-generating unit 300 is farther away from the rotating shaft 510 or the downward direction is referred to as "the other direction".

The ultrasonic wave-generating unit 300 may be coupled to the second frame 230 to move along a linear path.

In detail, the first frame 220 may have a linear track 221 formed in the moving direction of the ultrasonic wave-generating unit 300, and the second frame 230 may include a linear guide 231 moving along the linear track 221 while being inserted into the linear track 221. Accordingly, the movement of the ultrasonic wave-generating unit 300 may be guided along the linear path by the linear guide 231 of the second frame 230 moving along the linear track 221 of the first frame 220.

In this case, the linear guide 231 may be inserted into the linear track 221. In this case, the linear guide 231 may be rounded at one side thereof, to be easily inserted into the linear track 221.

In addition, the linear guide 231 and the linear track 221 may include a pair of linear guides and a pair of linear tracks, respectively. The pair of linear guides 231 may be coupled to the pair of linear tracks 221.

Meanwhile, referring to FIG. 3, a seating part 222 is formed on a bottom surface of the first frame 220 to protrude in the moving direction of the ultrasonic wave-generating unit 300, and a seating groove 232 is formed in a contact surface, which makes close contact with the bottom surface of the first frame 220, of the second frame 230, such that the seating part 222 is seated in the seating groove 232. The seating part 222 and the seating groove 232 prevent the first frame 220 and the second frame 230 from being biased, when the linear guide 231 moves along the linear track 221.

The elastic unit 400 generates elastic force allowing the ultrasonic wave-generating unit 300 to approach the rotating shaft 510. Accordingly, the ultrasonic wave-generating unit 300 is elastically supported at a present position, as long as the ultrasonic wave-generating unit 300 is not moved in the other direction by a rotating unit 500 to be described below.

The elastic unit 400 may generate elastic force that presses the second frame 230 in the one direction. In this case, the ultrasonic-wave generating unit 300 coupled to the second frame 230 may be pressed in the one direction. In this case, the elastic unit 400 may be a tensile spring for coupling the first frame 220 to the second frame 230.

The rotating unit 500 moves the ultrasonic wave-generating unit 300 to adjust the focal depth of the ultrasonic waves from the ultrasonic wave-generating unit 300. Such the rotating unit 500 has an outer circumferential surface making contact with a support unit 310 of the ultrasonic wave-generating unit 300, and has the shape of a section with a rotation radius gradually increased from the center of the rotating unit 500. For example, the rotating unit 500 may include the rotating shaft 510 and a cam 520. In this case, the rotating shaft 510 and the cam 520 may be formed integrally with each other.

The rotating shaft 510 may be disposed in the cartridge housing 200 in the longitudinal direction of the handpiece 100. The rotating shaft 510 may be formed through the cam 520 to be described below.

The cam 520 is disposed such that an outer circumferential surface of the cam 520 makes contact with the ultrasonic wave-generating unit 300, and coupled to the outer circumferential surface of the rotating shaft 510. For example, the cam 520 may have a shape surrounding the outer circumferential surface of the rotating shaft 510.

Accordingly, when the rotating shaft 510 rotates, the rotation radius of the cam 520, which makes contact with the ultrasonic wave-generating unit 300, is varied, so the ultrasonic wave-generating unit 300 may move. In addition, as the focal position of the ultrasonic waves irradiated from the ultrasonic wave-generating unit 300 moves, the focal depth of the ultrasonic waves from the ultrasonic wave-generating unit 300 may be adjusted.

For example, the cam 520 may have the shape of a section in which a rotation radius is gradually increased from the center of the rotating shaft 510. Accordingly, when the cam 520 is rotated as the rotating shaft 510 is rotated, the rotation radius of the cam 520 making contact with the ultrasonic wave-generating unit 300 is increased. Accordingly, the cam 520 may move the ultrasonic wave-generating unit 300 in the other direction.

In this case, the ultrasonic wave-generating unit 300 may move by the difference between the rotation radius at the initial position of the cam 520 making contact with the ultrasonic wave-generating unit 300 and the rotation radius at the final position of the cam 520 making contact with the ultrasonic wave-generating unit 300, when the rotation of the cam 520 is stopped. Accordingly, the focal depth of the ultrasonic waves from the ultrasonic wave-generating unit 300 may be adjusted.

As illustrated in FIG. 5, for another example, the cam 520 has the shape of a section in which the rotating radius is gradually increased from the center of the rotating shaft 510, and a plurality of contact protrusions 521 may be provided on the outer circumferential surface of the cam 520. Each of the plurality of contact protrusions 521 may have an arc shape in a cross section. In addition, the support unit 310 of the ultrasonic wave-generating unit 300 making contact with the outer circumferential surface of the cam 520 may have a contact part selectively contact to or separated from the plurality of contact protrusions 521. For example, the contact part may be a contact groove 311 recessed in the support unit 310. Accordingly, when the cam 520 is rotated as the rotating shaft 510 is rotated, the rotation radius of the cam 520 making contact with the ultrasonic wave-generating unit 300 is varied. Accordingly, the ultrasonic wave-generating unit 300 moves in the other direction.

In this case, when the rotation of the cam 520 is stopped, the ultrasonic wave-generating unit 300 may move in the other direction by the difference between the rotating radius "R1" of the contact protrusion 521, which first makes contact with the contact groove 311, and a rotating radius "RN" of the contact protrusion 521 which finally makes contact with the contact groove 311. Accordingly, the focal depth of the ultrasonic waves from the ultrasonic wave-generating unit 300 may be adjusted.

The plurality of contact protrusions 521 may protrude by a specific height from the outer circumferential surface of the cam 520.

Meanwhile, the rotating unit 500 may be rotated by the rotation adjusting unit 600.

The rotation adjusting unit 600 may be provided at a distal end of the rotating shaft 510 to apply force to the rotating shaft 510 such that the rotating shaft 510 is driven. As the rotation adjusting unit 600 rotates the rotating shaft 510, the cam 520 rotates together, while the rotating radius of the cam 520 making contact with the ultrasonic wave-generating unit 300 is varied, such that the ultrasonic wave-generating unit 300 moves in the other direction to adjust the focal depth of the ultrasonic waves from the ultrasonic wave-generating unit 300. In other words, as the cam 520 has the shape of a section in which the rotating radius thereof is gradually increased from the center of the rotating shaft 510, the rotating shaft 510 and the cam 520 may be rotated by the rotation adjusting unit 600. In this case, as the distance between the center of the rotating shaft 510 and the ultrasonic wave-generating unit 300 is increased, the focal depth of the ultrasonic waves from the ultrasonic wave-generating unit 300 is adjusted.

For example, the rotation adjusting unit 600 may be a driving unit such as a motor to drive the rotating shaft 510.

Referring to FIG. 2, for another example, the rotation adjusting unit 600 may be a knob 610 coupled to the distal end of the rotating shaft 510. A plurality of scales 611 may be marked in a circumferential direction on the outer surface of the knob 610 to indicate a rotating angle of the rotating shaft 510. Accordingly, when the user rotates the knob 610, the user may recognize the rotating angle of the rotating shaft 510 through the plurality of scales 611.

Meanwhile, the rotation of the cam 520 from the minimum rotating radius to the maximum rotating radius may be restricted by the support unit 310 and a restriction protrusion 522. The restriction in the rotation of the cam 520 is to prevent the cam 520 from being reversely rotated. In addition, the restriction in the rotation of the cam 520 is to prevent the tensile spring, which serves as the elastic unit 400, from being excessively stretched, and to prevent the ultrasonic wave-generating unit 300 from suddenly moving an excessively long distance, as the rotating radius of the cam 520 is suddenly increased from the minimum rotating radius of the cam 520 to the maximum rotating radius of the cam 520.

The support unit 310 has a structure protruding toward the cam 520 from the contact surface with the ultrasonic wave-generating unit 300 which is in contact with the outer circumferential surface of the cam 520. For example, the support unit 310 may have an equilateral trapezoidal structure having opposite side surfaces inclined, but the inventive concept is not limited thereto. The contact groove 311 may be formed in the contact surface of the support unit 310 making contact with the cam 520, such that the plurality of contact protrusions 521 selectively make contact with the contact groove 311 or is separated from the contact groove 311.

A restriction protrusion 522 is locked to the support unit 310 to restrict the rotating radius of the cam 520 while ranging from the minimum rotating radius of the cam 520 to the maximum rotating radius of the cam 520, thereby restricting the focal depth of the ultrasonic wave, which is generated from the ultrasonic wave-generating unit 300, while ranging from the minimum focal depth to the maximum focal depth. The restriction protrusion 522 may protrude to be longer at a position connected to the contact protrusion 521 having the minimum rotating radius. Accordingly, when the cam 520 rotates while ranging from the minimum rotating radius to the maximum rotating radius, the restriction protrusion may be supported on a side surface of the support unit 310. Accordingly, the rotation of the cam 520 may be restricted while ranging from the minimum rotating radius toward the maximum rotating radius.

Meanwhile, the rotation of the rotating unit 500 may be locked or unlocked by the locking unit (not illustrated).

For example, the locking unit (not illustrated) may include a pressing device to press the rotating unit 500 to lock the rotation of the rotating unit 500 or to release pressure applied to the rotating unit 500 to unlock the rotation of the rotating unit 500. For example, the pressing device may include an actuator, but the inventive concept is not limited thereto.

For another example, the locking unit (not illustrated) may include a latch device having a latch protrusion locked to the contact protrusion 521 to lock the rotation of the rotating unit 500 or unlocked from the contact protrusion 521 or a button-type lock device.

Hereinafter, an operation example of the ultrasonic wave-generating unit to adjust the focal depth of the ultrasonic waves will be described.

Figure 6:
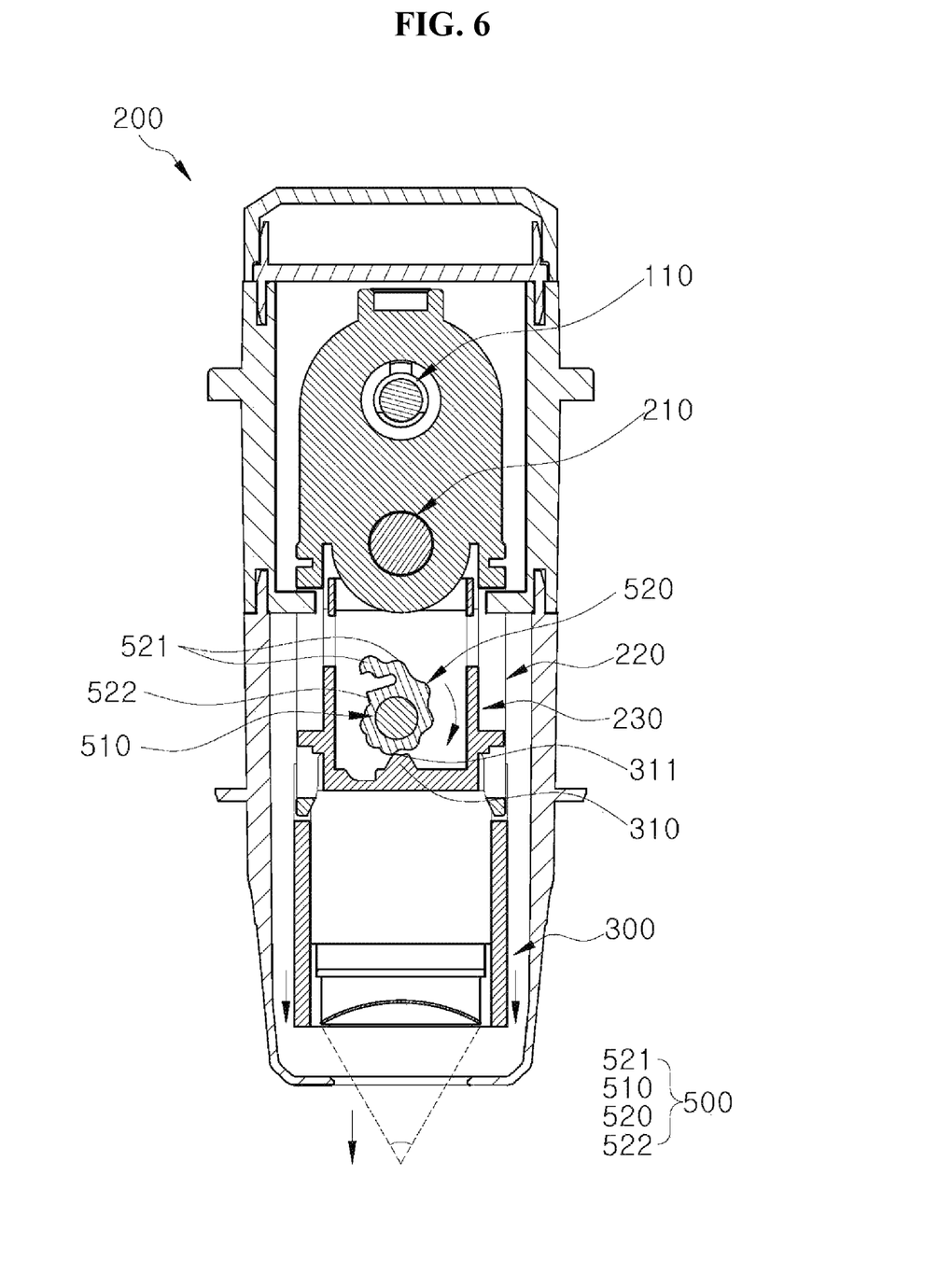
FIG. 6 is a view illustrating ultrasonic waves-generating unit of FIG. 4 moved in another direction.

FIG. 6 is a view illustrating an ultrasonic wave-generating unit of FIG. 4 moved in another direction.

First, referring to FIGS. 2 and 4, as the elastic unit 400 presses the second frame 230 in the one direction, the second frame 230 is pressed and fixed in the one direction. In link to the above operation, even the ultrasonic wave-generating unit 300 coupled to the second frame 230 is pressed and fixed together in the one direction by the elastic unit 400. In this case, the contact protrusion 521, which has the minimum rotating radius, of the plurality of contact protrusions 521 of the cam 520 may first make contact with and fixed to the contact groove 311 of the ultrasonic wave-generating unit 300.

Next, referring to FIG. 6, as the rotation adjusting unit 600 is rotated, the rotating shaft 510 is rotated at a specific angle, and even the cam 520 is rotated at the specific angle in link to the above operation. In this case, the rotation adjusting unit 600 may be manually rotated by the user or may be automatically rotated by a driving motor.

Accordingly, the contact protrusion 521, which has a rotating radius larger than the minimum rotating radius, of the plurality of contact protrusions 521 of the cam 520 makes contact with the contact groove 311 of the ultrasonic wave-generating unit 300.

Accordingly, as the rotating radius of the cam 520 making contact with the ultrasonic wave-generating unit 300 is increased, the ultrasonic wave-generating unit 300 is moved in the other direction. In this case, the movement of the ultrasonic wave-generating unit 300 in the other direction may be guided along the linear path by the linear guide 231 of the second frame 230 moving along the linear track 221 of the first frame 220.

Next, when the rotating shaft 510 is stopped, the cam 520 is stopped in link to the stop of the rotating shaft 510. In this case, the ultrasonic wave-generating unit 300 may be moved by the difference between the rotating radius "R1" of the contact protrusion 521 of the cam 520, which first makes contact with the contact groove 311 of the ultrasonic wave-generating unit 300, and a rotating radius "RN" of the contact protrusion 521 of the cam 520 which finally makes contact with the contact groove 311 of the ultrasonic wave-generating unit 300.

Accordingly, the focal depth of the ultrasonic waves from the ultrasonic wave-generating unit 300 may be adjusted by the movement distance of the ultrasonic wave-generating unit 300.

Figure 7:
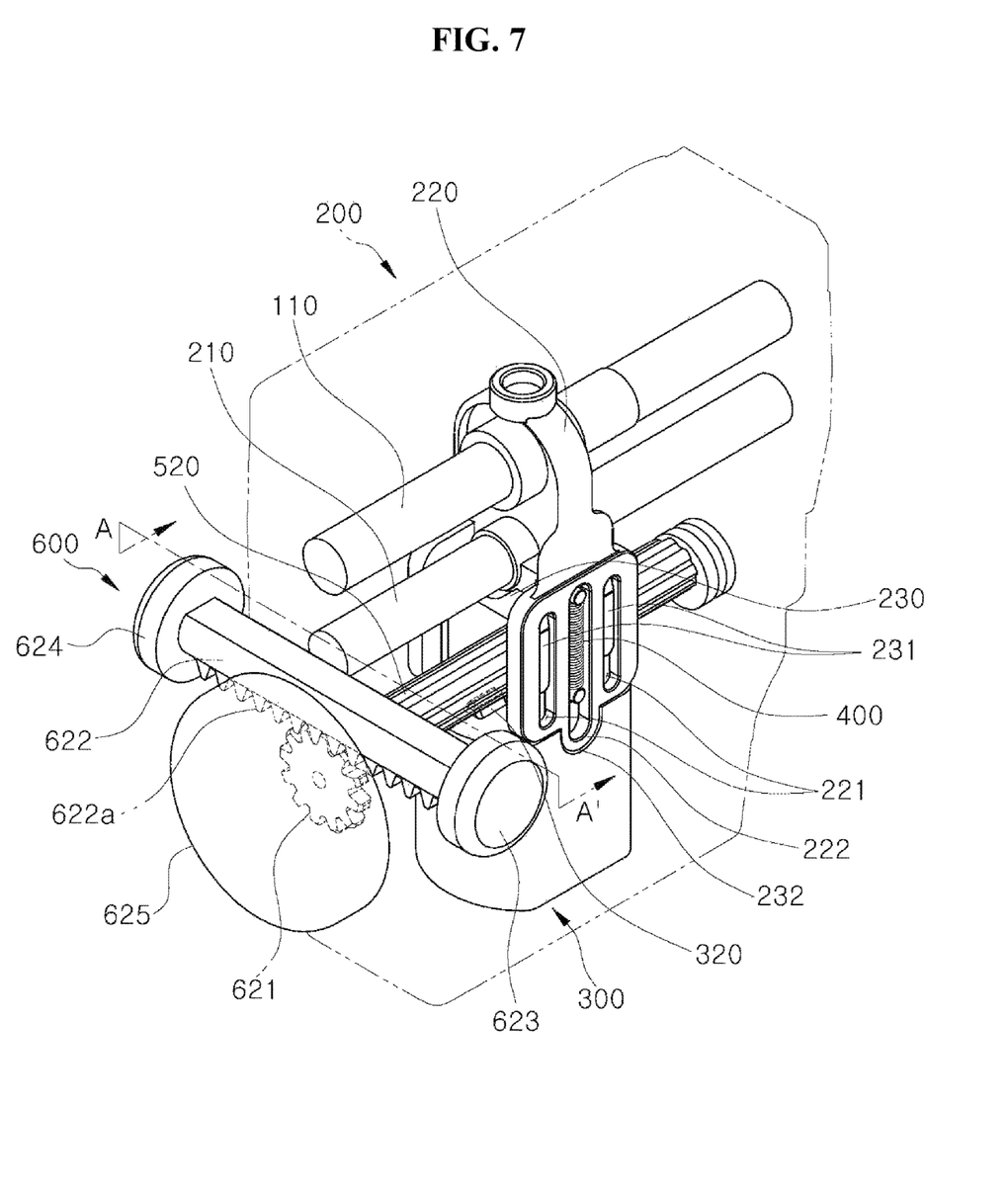
FIG. 7 is a perspective view illustrating an operating button, according to an embodiment of the inventive concept.
Figure 8:
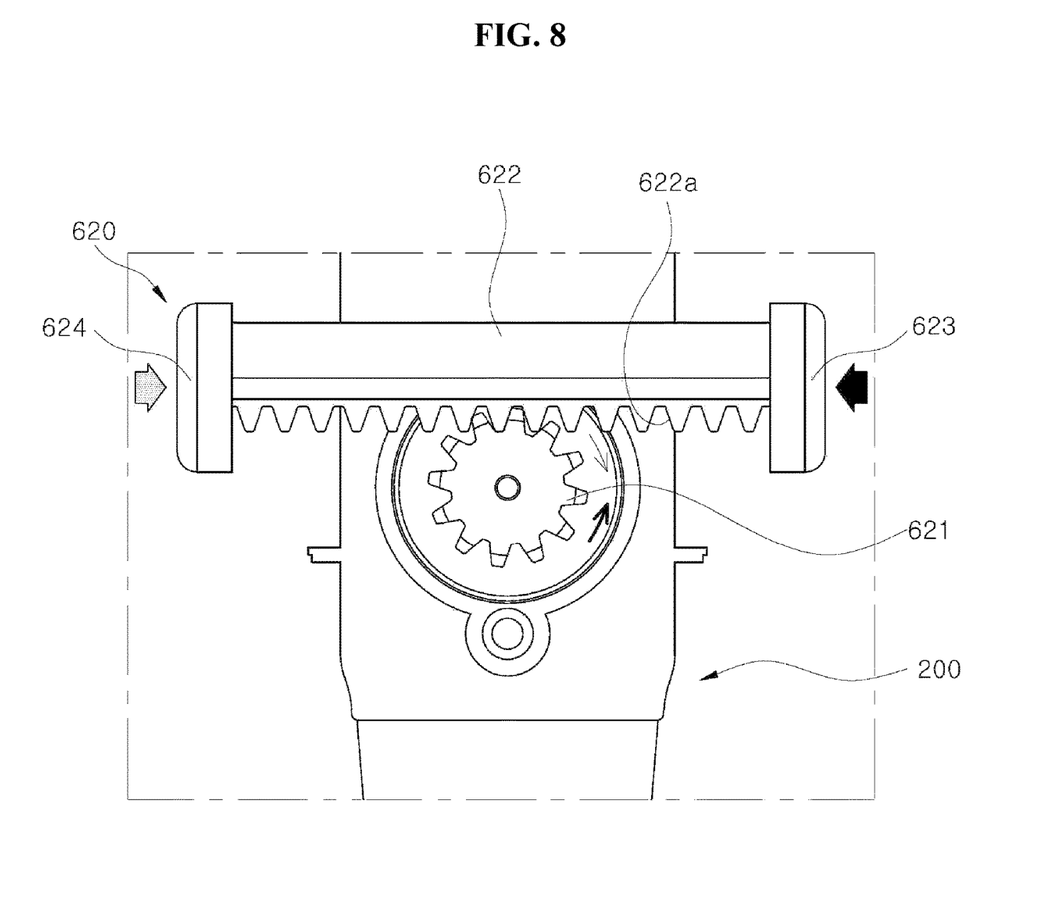
FIG. 8 is a cross-sectional view taken along line A-A' of FIG. 7.

FIG. 7 is a perspective view illustrating an operating button according to an embodiment of the inventive concept, and FIG. 8 is a cross-sectional view taken along line A-A' of FIG. 7.

As illustrated in FIGS. 7 and 8, the rotation adjusting unit 600 may be an operating button 620 provided at a distal end of the rotating shaft 510.

The operating button 620 may include a pinion gear 621 coupled to the distal end of the rotating shaft 510, an operating rod 622 having a rack gear 622a geared with the pinion gear 621, and a first pusher 623 and a second pusher 624 coupled to opposite ends of the operating rod 622. In this case, the rack gear 622a may be formed in a longitudinal direction of the operating rod 622.

For example, when the first pusher 623 is pushed, the operating rod 622 is moved from the first pusher 623 to the second pusher 624, such that the rack gear 622a rotates the pinion gear 621 in the one direction, and the rotating shaft 510 coupled to the pinion gear 621 is rotated in the one direction together.

For another example, when the second pusher 624 is pushed, the operating rod 622 is moved from the second pusher 624 to the first pusher 623, such that the rack gear 622a rotates the pinion gear 621 in the other direction, and the rotating shaft 510 coupled to the pinion gear 621 is rotated in the other direction together.

Meanwhile, the pinion gear 621 may be received in a button housing 625, and the operating rod 622 may be geared with the pinion gear 621 passing through the button housing 625.

According to the inventive concept, according to an embodiment of the inventive concept, the ultrasonic wave-generating unit may adjust the focal depth of the ultrasonic waves depending on the target depth of the skin.

According to an embodiment of the inventive concept, the device for generating the ultrasonic waves may adjust the focal depth of the ultrasonic waves depending on the target depth of the skin.

The effects of the inventive concept are not limited to the above, but other effects, which are not mentioned, will be apparently understood to those skilled in the art.

Although an embodiment of the inventive concept are described with reference to the accompanying drawings, it will be understood by those skilled in the art to which the inventive concept pertains that the inventive concept can be carried out in other detailed forms without changing the scope and spirit or the essential features of the inventive concept. Therefore, the embodiments described above are provided by way of example in all aspects, and should be construed not to be restrictive.

What is claimed is:

1. A device for generating ultrasonic waves having an adjustable focal depth for the ultrasonic waves, the device comprising:
   a handpiece;
   a cartridge housing detachably coupled to the handpiece;
   an ultrasonic wave generator disposed in the handpiece or the cartridge housing, wherein the ultrasonic wave generator is configured to generate the ultrasonic waves;
   a rotatable cam having a plurality of contact protrusions provided on an outer circumferential surface of the rotatable cam, wherein the plurality of contact protrusions correspond to a plurality of radiuses, wherein the rotatable cam is configured to be rotated to a plurality of positions corresponding to the plurality of radiuses and thereby move the ultrasonic wave generator to different focal depths, wherein a first position of the rotatable cam corresponding to a first radius corresponds to a first focal depth for the ultrasonic waves generated by the ultrasonic wave generator, and wherein a second position of the rotatable cam corresponding to a second radius corresponds to a second focal depth for the ultrasonic waves generated by the ultrasonic wave generator, wherein the first radius is different form the second radius, and wherein the first focal depth is different from the second focal depth; and
   an actuator configured to apply force which rotates the rotatable cam to the plurality of positions.

2. The device of claim 1, wherein the actuator comprises a motor, a knob, or a button.

3. The device of claim 1,
   wherein the ultrasonic wave generator comprises a support having a contact part which is configured to make contact with and be separated from the plurality of contact protrusions.

4. The device of claim 3, wherein the contact part is a contact groove recessed in the support.

5. The device of claim 3, further comprising:
   a lock configured to lock and unlock rotation of the cam.

6. The device of claim 2, wherein the cam includes a restriction protrusion which is configured to prevent rotation of the cam in one direction while the cam is in a position corresponding to a minimum radius out of the plurality of radiuses.

7. The device of claim 1, further comprising:
an elastic unit configured to generate elastic force which opposes a moving direction of the ultrasonic wave generator.

8. The device of claim 7, further comprising:
a first frame; and
a second frame coupled to the first frame and to the ultrasonic wave generator, wherein the second frame is movable in the moving direction of the ultrasonic wave generator.

9. The device of claim 8, wherein the first frame includes a linear track formed in the moving direction of the ultrasonic wave generator; and
wherein the second frame includes a linear guide configured to move along the linear track.

10. The device of claim 9, wherein the elastic unit is a spring which connects the first frame to the second frame.

11. The device of claim 8, further comprising:
a driving device disposed in the handpiece; and
a main shaft having one end coupled to the driving device and an opposite end passing through the first frame;
wherein the driving device is configured to move the main shaft in a longitudinal direction of the handpiece.

12. The device of claim 11, wherein the driving device comprises an actuator.

13. The device of claim 11, wherein the driving device comprises a motor.

* * * * *